(12) United States Patent  
Gutman

(10) Patent No.: US 9,013,688 B2  
(45) Date of Patent: Apr. 21, 2015

(54) METHOD FOR OPTICAL INSPECTION, DETECTION AND ANALYSIS OF DOUBLE SIDED WAFER MACRO DEFECTS

(71) Applicant: May High-Tech Solutions Ltd., Or Yehuda (IL)

(72) Inventor: Moshe Gutman, Modiin (IL)

(73) Assignee: May High-Tech Solutions Ltd. (IL)

( * ) Notice: Subject to any disclaimer, the term of this patent is extended or adjusted under 35 U.S.C. 154(b) by 0 days.

(21) Appl. No.: 14/071,354

(22) Filed: Nov. 4, 2013

(65) Prior Publication Data

US 2014/0064599 A1   Mar. 6, 2014

Related U.S. Application Data

(62) Division of application No. 13/476,872, filed on May 21, 2012, now Pat. No. 8,576,393.

(30) Foreign Application Priority Data

May 19, 2011   (IL) .......................................... 213025

(51) Int. Cl.

| | |
|---|---|
| G01N 21/00 | (2006.01) |
| G06T 7/00 | (2006.01) |
| G01N 21/47 | (2006.01) |
| G01N 21/95 | (2006.01) |
| G01N 21/88 | (2006.01) |

(52) U.S. Cl.
CPC .............. *G06T 7/0004* (2013.01); *G01N 21/47* (2013.01); *G01N 21/9501* (2013.01); *G01N 2021/8825* (2013.01)

(58) Field of Classification Search
CPC ... G01N 21/9501; G01N 21/47; G01N 21/94; G01N 2021/8825; G01N 21/8806; G01N 21/9503; G01N 2021/8822; G06T 7/0004; H01L 22/12
USPC ............................................ 356/237.1–237.5
See application file for complete search history.

(56) References Cited

U.S. PATENT DOCUMENTS

| | | | |
|---|---|---|---|
| 6,016,562 A * | 1/2000 | Miyazaki et al. ............. | 714/724 |
| 6,654,109 B2 | 11/2003 | Li et al. | |
| 2004/0207836 A1* | 10/2004 | Chhibber et al. .......... | 356/237.4 |
| 2007/0268484 A1* | 11/2007 | Matsui ....................... | 356/237.3 |
| 2009/0091750 A1* | 4/2009 | Urano et al. ............... | 356/237.3 |

* cited by examiner

*Primary Examiner* — Tri T Ton  
(74) *Attorney, Agent, or Firm* — Kolisch Hartwell, P.C.

(57) ABSTRACT

A method of automatic optical self-contained inspection for detection of macro defects of sub-pixel defect size in pattern wafers and non-pattern wafers is based on surface light scattering color-intensity computerized analysis. The method includes setting-up initial calibration and deriving correction data. A wafer image is acquired and rendered and compensated for lighting intensity and optical sensor sensitivity color spectra biases and spatial variances prior to displaying the inspection results.

17 Claims, 2 Drawing Sheets

METHOD FOR OPTICAL INSPECTION, DETECTION AND ANALYSIS OF DOUBLE SIDED WAFER MACRO DEFECTS

CROSS-REFERENCES

The present application is a divisional of U.S. patent application Ser. No. 13/476,872, filed May 21, 2012, and issued as U.S. Pat. No. 8,576,393 on Nov. 5, 2013, which in turn claims the benefit of Israeli Patent Application No. 213025, filed May 19, 2011.

FIELD OF THE INVENTION

The present invention pertains in general to the manufacture of semiconductor integrated circuit devices. More specifically, it relates to quality inspection of wafer processing and, in particular, to a method and apparatus for detection and characterization of defects, and working order assessment of fab processing operation.

BACKGROUND OF THE INVENTION

It often occurs that during device manufacture in fab at most of process steps (i.e. Litho, handling, etching, deposition, layers growth, metallization and others) defects are created as a result of machine malfunction and/or process flow instability caused by chemicals or other delivered materials participating the process.

The presence of defects may impair the quality of the final product. The yield and productivity are adversely affected if the defect presence is not detected in time. Therefore, inspecting wafers for defects is widely implemented in semiconductor manufacturing processes and procedures.

When defects are detected in time, it may be possible to take appropriate remedial action, such as defected wafer re-processing, or defective wafer exclusion from consequent process flow. Close monitoring and awareness of the operational quality of the processing tool and its maintenance initiation are attained as well.

Prior art methods are known that perform surface inspection by contrast variation analysis during the manufacturing process. In contrast thereto, the method according to the invention may also be implemented off-process, i.e. using a standalone inspection tool may or may not be integrated with the host system. Furthermore, unlike known inspection tools, the invention performs instantaneous imaging and illumination of the entire wafer.

There is still further need for a method and apparatus capable of fast execution of the imaging and computation tasks of the defects detection processes during fabrication, to permit incorporation of inspection processes in the host tool production cycle timeframe. Integration of the inspection tool in the host system requires instantaneous or almost instantaneous image acquisition of the wafer surface under test, and accordingly illumination of the complete wafer sample, while accommodating the constraints of the parent tool space, operation dynamics and cycle. Moreover, tailored, task-oriented defects detection and optimized image processing manipulation algorithms are needed.

Furthermore, there is a need for metrology quantification and characterization of detected defects and appropriate database accumulation for consequent process tool integrity evaluation and preventive maintenance prompting.

WO 2006/046236 in the name of the present Applicant discloses an automatic optical inspection apparatus and method for residue detection on polished wafers, including an illumination source capable of instantaneous entire wafer surface illumination, a color digital camera, encompassing the entire wafers surface without eclipse, in a duple of consecutive, properly delayed imaging shots and provides appropriate image resolution for tiny residue detection, computation means, implementing image processing and manipulation algorithms to enable residue detection and characterization, logic and command operations execution and camera control. The computation means accumulates a database of on-line created wafer images and wafer residue defects, the computation means providing for inspection tool worthiness monitoring, wafer handling and transportation means.

SUMMARY OF THE INVENTION

In accordance with a first aspect of the present invention there is provided an apparatus for simultaneous optical inspection and detection of defects on opposite surfaces of a wafer, the apparatus comprising:

a circumferential dark field source and a bright illumination source both configured to illuminate simultaneously opposite surfaces of the wafer for both bright field and dark field applications;

an optical sensor disposed normal to the wafer surface and to the illumination source for capturing light reflected from the wafer surface and producing a sensor signal having sufficient resolution for detection of defects; and a processing unit coupled to the optical sensor for processing the sensor signal in accordance with stored instructions for accumulating data representative of an image of the wafer and defects, and for providing an indication of defects.

In accordance with a second aspect of the invention there is provided a method of automatic optical self-contained inspection for detection of macro defects of sub-pixel defect size in pattern wafers and non-pattern wafers based on surface light scattering color-intensity computerized analysis, the method comprising:

setting-up initial calibration and correction data derivation;

wafer image acquisition and rendering;

compensating for lighting intensity and optical sensor sensitivity color spectra biases and spatial variances; and displaying the inspection results.

In more detail, the invention provides an automatic optical inspection apparatus for detection of different kinds of defects in wafers, comprising an illumination source, capable of instantaneous entire wafer surface illumination, optical sensor, encompassing the entire wafers surface, in a duple of consecutive, properly delayed imaging shots and providing appropriate image resolution for macro defects detection, computation means, implementing image processing and manipulation algorithms to enable defects detection and characterization, logic and command operations execution, and optical sensor control, said computation means accumulating an on-line created wafer images and wafer defects data base, said computation means providing for inspection tool worthiness monitoring, wafer handling and transportation means, and an operator for controlling inspection process and results supervision and on-time process flow alternation or interruption to efficiently and timely incorporate and carry out the inspection process findings and prompts.

The invention further provides a method of automatic optical self-contained inspection for detection of defects in patterned and non-patterned wafers with sub-pixel defect size, effective spatial sensitivity, based on light scattering from the surface of the wafer-under-inspection, computerized color-intensity analysis, comprising the steps of setting-up an initial calibration and correction data derivation, wafer image acquisition and rendering, compensating for lighting intensity and camera sensitivity color spectra biases and spatial variances, self-contained image scattering intensity analysis for amplitude and color-ratio comparison, defects covered areas discriminating against the patterned wafer area portions, and image rectification and on-screen presentation of inspection results containing wafer-under-inspection zoomed image and corresponding emphasized detected image.

The optical sensor may be any optical device containing any combination of controlled optical and electronic materials that can sense light. The image created by the optical sensor is computed and sent to the tool controller. For example the optical sensor can be a digital camera.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
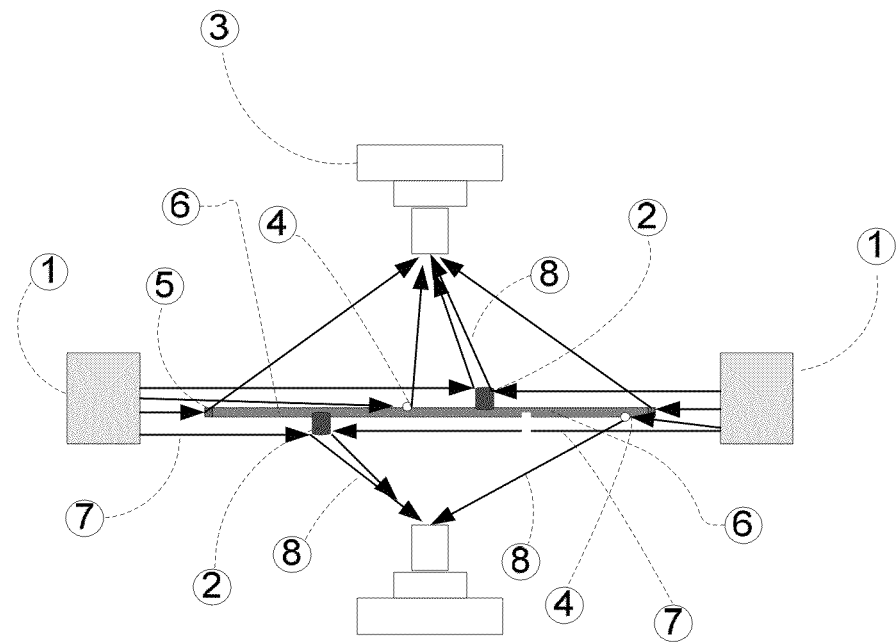
FIG. 1 is a schematic cross-section of a dark field system.

FIG. 1 is a schematic cross-section of a Dark Field system. An annular illumination source includes an illumination source disposed within a circumferential ring 1 thereby producing an illumination ring in the middle of which a wafer 6 is located. The annular illumination source produced a collimated beam of light 7. When the beam meets a 3-dimensional defect 2 projecting out of an upper or lower surface the wafer, a scratch 4 in the wafer surface or a defect in the wafer edge 5, the beam is reflected back as a reflected beam 8 to an optical sensor 3. Since the illumination source beam of light is substantially parallel to the wafer, the wafer pattern is not reflected back to the optical sensor 3. Since the wafer is located at the center of the circumferential ring, the beam of light created by the illumination source is able to strike defects on both the front and rear surfaces of the wafer and the image acquisition is made simultaneously for both wafer surfaces.

Figure 2:
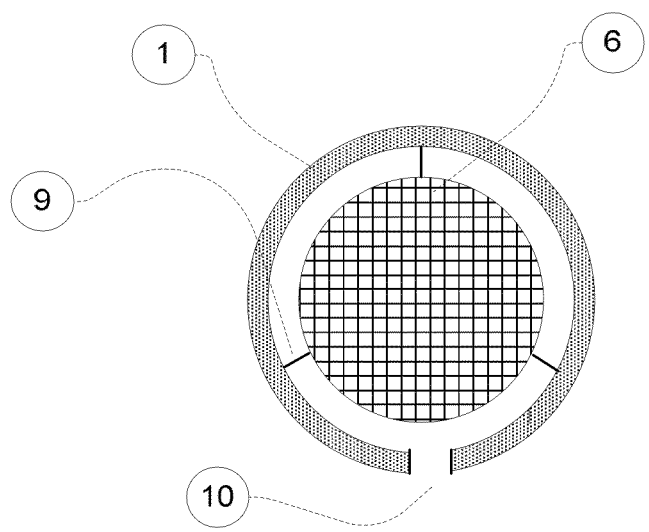
FIG. 2 is a plan view showing schematically placement of a wafer in the center of a circumferential ring.

FIG. 2 is a plan view showing how the wafer is placed in the center of the circumferential ring. In one embodiment, the circumferential ring is not totally closed but has an opening 10. The inspection tool includes a robot arm (not shown) that is dimensioned to fit into opening 10. The robot arm is aligned with the opening 10 while supporting the wafer under its lower surface, approaches the robot arm from above the ring and lays the wafer on pins 9. It is then lowered still further until it loses contact with the lower surface of the wafer, whereupon it is withdrawn from the opening 10 and returns to its original location. Following this operation only the wafer surfaces are exposed to the optical sensors. In an alternative embodiment, the circumferential ring is totally closed. In this case the robotic arm supports the wafer from above (for example, by suction) and lays it on the protruding pins.

Figure 3:
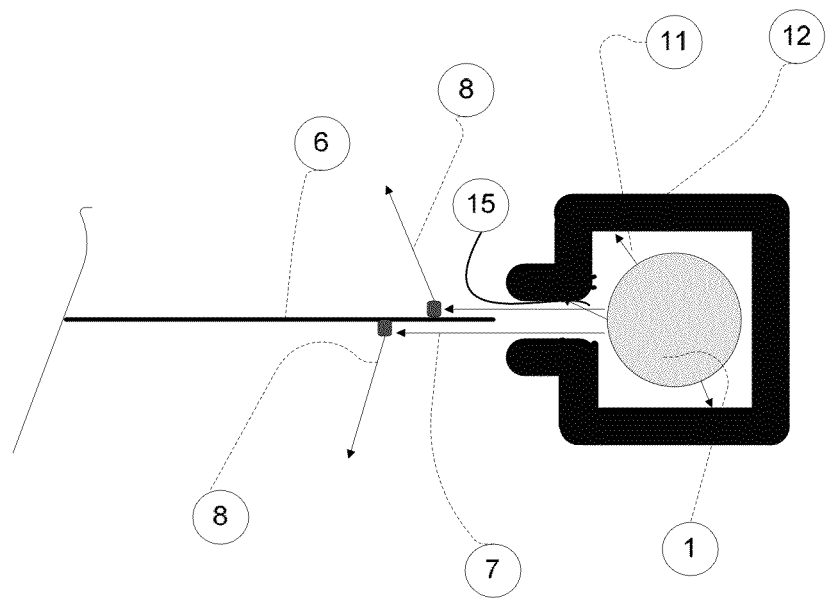
FIG. 3 illustrates schematically a cross-section of the circumferential illumination source while applying the dark field application test.

FIG. 3 illustrates a cross-section of the circumferential illumination source while applying the Dark Field application test. The illumination source may be a round fluorescent lamp or LED etc. and is located within the circumferential ring 1, whose internal surface is coated by a light-absorbent material 12. Light beams that are not parallel 11 to the wafer surface are absorbed by this material 12. The parallel light beams 7 pass through a slot 15 and strike the defect at the wafer surface, which reflects the light beam as a reflected beam 8 to the optical sensor. The geometrical shape, specifically the width and shape of the slot, determines how much of the light beam is parallel to the wafer.

Figure 4:
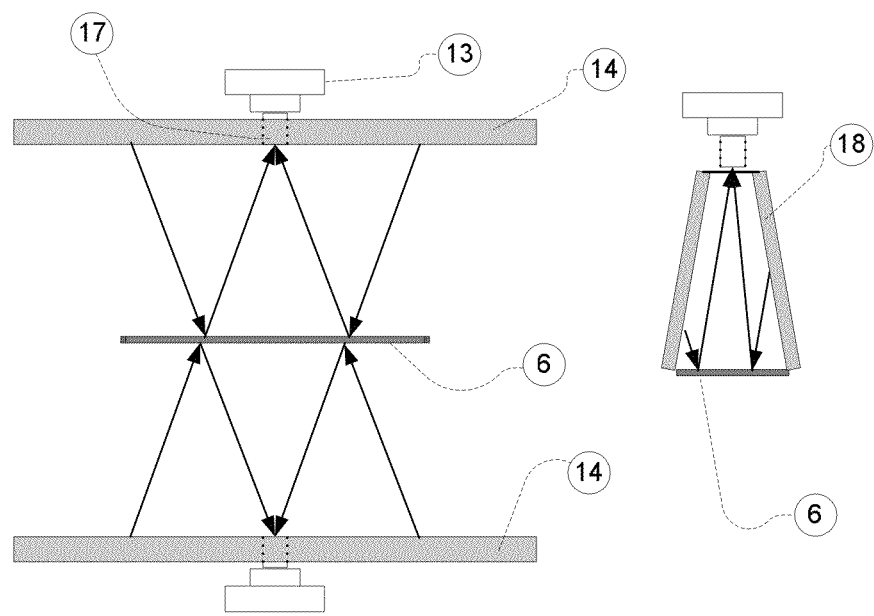
FIG. 4 illustrates schematically the bright field application test.

FIG. 4 illustrates the Bright Field application test. The aim of the Bright field application is to detect defects such as scratches that are not 3-dimensional. It detects defects that are characterized by a change in color intensity or color shade. The changes in colors may be indicative of changes in thickness occurring during the wafer process. The Bright Field illumination source is made by an illumination board 14 that directs homogenous light with a unified intensity on the wafer surface. A hole 17 in the center of the board allows the optical sensor to identify the wafer surface and identify changes and shades in the wafer color. Since the optical sensor 13 that is located in the center of the illumination board 14 does not illuminate the center of the illumination board 14, it creates a shadow at the wafer center and prevents image detection at this specific location. In case it is required to check this location also, the robot can move the wafer or the optical sensor and the light board to a different location and expose the shadow location to the optical sensor. The illumination source may be constituted by a trimmed cone 18 with the optical sensor 13 being located toward the apex of the illumination cone and the wafer being located at the bottom side of the homogenous illumination source.

It is to be noted that the appended claims constitute an integral component of the description and features that are described in the claims are to be construed as part of the detailed description to any extent necessary to comply with the requirements of enablement and sufficiency of disclosure.

The invention claimed is:

1. A method of automatic optical self-contained inspection for detection of macro defects of sub-pixel defect size in pattern wafers and non-pattern wafers based on surface light scattering color-intensity computerized analysis, the method comprising:

setting-up initial calibration and correction data derivation;

wafer image acquisition and rendering;

compensating for lighting intensity and optical sensor sensitivity color spectra biases and spatial variances; and displaying the inspection results;

wherein wafer image acquisition and rendering includes:

illuminating opposite surfaces of the wafer simultaneously with a circumferential dark field source having an optical axis that is normal to the wafer and that is disposed around a periphery of the wafer, wherein the circumferential dark field source is disposed within a circumferential ring having an internal surface coated by a light-absorbent material for absorbing light beams that are not parallel to the wafer surface;

illuminating respective opposite surfaces of the wafer with a bright illumination source;

disposing on opposite surfaces of the wafer a pair of optical sensors normal to both the wafer surfaces and to the bright illumination source, both of said sensors having an optical axis that is coaxial with the optical axis of the circumferential dark field source, and using said sensors to capture light reflected from the wafer surface and to produce a sensor signal having sufficient resolution for detection of surface defects.

2. The method as claimed in claim 1, further comprising classifying macro defects according to a measure of their potential harm.

3. The method as claimed in claim 1, further comprising:
integrating defect data obtained from inspection of inter-lot and intra-lot wafers; and
performing integrative analysis.

4. The method as claimed in claim 1, further comprising presenting inspection results in a Man Machine Interface configured to allow a process operator to scroll through wafers in a lot-under-inspection or stored images and results relating to defects of any previously inspected lot.

5. The method as claimed in claim 1, including compensating for variations in the optical sensor and illumination source luminance.

6. The method as claimed in claim 1, further comprising threshold detection of spatially variable defects, thus implementing CFAR and enhancing inspection sensitivity.

7. The method as claimed in claim 1, further comprising analyzing pixel color ratios for verification of detected defects.

8. The method as claimed in claim 1, further comprising detecting artifacts that are not defects, including determining pixel color ratios that distinguish said artifacts from genuine defects based on scattering color spectra of a specific material.

9. The method as claimed in claim 1, further comprising detection and quantification of patterned wafers surface over-defects presence.

10. The method as claimed in claim 1, including wherein wafer image acquisition and rendering further includes simultaneous image acquisition of both the front and rear surfaces of the wafer and minimization of the image's perspective geometrical distortions.

11. The method as claimed in claim 10, wherein wafer image acquisition and rendering further includes arranging the bright illumination source and the optical sensor coaxially.

12. The method as claimed in claim 1, including disposing the optical sensor within a hole made in the bright field illumination source.

13. The method as claimed in claim 1, including:
providing a slot in the circumferential ring, and
dimensioning the slot to allow light beams that are parallel to the wafer surface to pass through the slot and strike a defect at the wafer surface.

14. The method as claimed in claim 13, including aligning the slot with a periphery of the wafer.

15. The method as claimed in claim 1, including providing for each of the bright illumination sources an illumination board for directing homogenous light with a unified intensity from the respective bright illumination source on to a respective surface of the wafer.

16. The method as claimed in claim 15, including disposing the optical sensors in a hole in a respective one of the illumination boards.

17. The method as claimed in claim 1, including:
configuring each of the bright illumination sources as an illumination cone; and
locating the respective optical sensor toward an apex of the illumination cone with the wafer being located at a bottom side of the bright illumination source.

* * * * *